(12) United States Patent
Frazer et al.

(10) Patent No.: US 9,751,234 B2
(45) Date of Patent: Sep. 5, 2017

(54) WOOD TREATMENT

(71) Applicant: WQI LIMITED, Rotorua (NZ)

(72) Inventors: Frank William Frazer, Auckland (NZ); Clive John Bolt, Auckland (NZ); Neil Raymond Edmonds, Auckland (NZ)

(73) Assignee: CODIL LIMITED, Ashburton (NZ)

( * ) Notice: Subject to any disclaimer, the term of this patent is extended or adjusted under 35 U.S.C. 154(b) by 0 days.

(21) Appl. No.: 14/765,582

(22) PCT Filed: Sep. 12, 2013

(86) PCT No.: PCT/IB2013/058470
§ 371 (c)(1),
(2) Date: Aug. 4, 2015

(87) PCT Pub. No.: WO2014/122508
PCT Pub. Date: Aug. 14, 2014

(65) Prior Publication Data
US 2015/0367526 A1    Dec. 24, 2015

(30) Foreign Application Priority Data

Feb. 7, 2013 (NZ) ........................... 606755

(51) Int. Cl.

| | |
|---|---|
| *B27K 3/52* | (2006.01) |
| *C09D 15/00* | (2006.01) |
| *B27K 3/16* | (2006.01) |
| *A01N 43/653* | (2006.01) |
| *A01N 53/00* | (2006.01) |
| *A01N 55/04* | (2006.01) |
| *A01N 55/08* | (2006.01) |
| *B01J 31/04* | (2006.01) |

(52) U.S. Cl.
CPC .............. *B27K 3/52* (2013.01); *A01N 43/653* (2013.01); *A01N 53/00* (2013.01); *A01N 55/04* (2013.01); *A01N 55/08* (2013.01); *B01J 31/04* (2013.01); *B27K 3/16* (2013.01); *C09D 15/00* (2013.01); *Y10T 428/662* (2015.04)

(58) Field of Classification Search
None
See application file for complete search history.

(56) References Cited

U.S. PATENT DOCUMENTS

| | | | | |
|---|---|---|---|---|
| 3,008,847 | A | * 11/1961 | La Berge | ............... C09D 5/002 |
| | | | | 428/328 |
| 3,900,620 | A | * 8/1975 | Gilman | ................... B05D 7/06 |
| | | | | 427/325 |
| 4,331,575 | A | * 5/1982 | Feldman | ................... C09F 9/00 |
| | | | | 106/264 |
| 4,977,186 | A | 12/1990 | Gruening | |
| 5,017,669 | A | 5/1991 | Young | |
| 5,320,872 | A | 6/1994 | McNeel et al. | |
| 6,352,583 | B1 | 3/2002 | Goettsche et al. | |
| 6,503,306 | B1 | 1/2003 | Watkins | |
| 6,753,016 | B2 | * 6/2004 | Ghosh | ..................... B27K 3/16 |
| | | | | 424/604 |
| 2009/0280345 | A1 | 11/2009 | Maynard et al. | |
| 2014/0147691 | A1 | 5/2014 | Humphrey et al. | |

FOREIGN PATENT DOCUMENTS

| | | |
|---|---|---|
| EP | 0328323 B1 | 4/1992 |
| EP | 0344161 B1 | 9/1993 |
| NZ | 519693 A | 8/2003 |
| NZ | 538446 A | 1/2008 |
| WO | 2013000037 A1 | 1/2013 |

OTHER PUBLICATIONS

Dawson, B.S.W. et al., 'Resin bleed after painting from radiata pine boards treated with tributyltin naphthenate (light organic solvent preservative) or copper, chromium and arsenic compounds (waterborne preservative)', Holz als Roh- und Werkstoff, 2002, vol. 60, pp. 18-24.
Gorkum, R.V. et al., 'The oxidative drying of alkyd paint catalysed by metal complexes', Coordination Chemistry Reviews, 2005, vol. 249, pp. 9-39.
First Examination Report dated Sep. 19, 2013 from the New Zealand Intellectual Property Office.

* cited by examiner

*Primary Examiner* — Nathan T Leong
(74) *Attorney, Agent, or Firm* — Sughrue Mion, PLLC

(57) ABSTRACT

Compositions comprising one or more autoxidative catalysts for treating wood and reducing or preventing resin show-through or resin-bleed or both.

30 Claims, No Drawings

WOOD TREATMENT

This application is a National Stage of International Application No. PCT/IB2013/058470 filed Sep. 12, 2013, claiming priority based on New Zealand Patent Application No. 606755, filed Feb. 7, 2013, the contents of all of which are incorporated herein by reference in their entirety.

FIELD OF THE INVENTION

The present invention relates to compositions for treating wood, and in particular to compositions comprising one or more autoxidative catalysts, such as those commonly used as paint driers, and their use for reducing or preventing resin show-through or resin-bleed or resin show-through and resin-bleed, particularly in pine.

BACKGROUND OF THE INVENTION

Pine species such as *Pinus radiata* produce suitable timber, when dried, to allow high quality paint treatments for exterior uses, such as weatherboards, fascia and other wood cuts.

Pine timber which exhibits strong resinous features at or near the surface to be painted can lead to an undesirable reduction in the quality of the paint finish. Resinous features may take the form of broad latewood bands, resin pockets, local or widespread resinous areas, which are largely associated with tree growth stresses, such as drought, wind, or insect or other damage.

The weathering properties of painted resinous wood are generally poor because of features such as resin bleed, where wood resin may exude through the paint film to produce unsightly deposits on the surface; or resin show-through, where footprints of the wood resinous areas are apparent without any resin breakthrough the paint surface. Resin show-through is potentially more common, as it may occur in moderately resinous wood and may be evident within the first year or two after painting. In comparison, resin bleed is associated with extremely resinous wood.

At low magnifications, resin show-through is observed as micro-blistering, bubbling, or in severe cases a crocodile skin appearance, of the painted surface. Visually, it is observed as paint shade differences revealing the resinous areas. Generally the paint in the resinous areas appears bleached or washed out and these effects occur because of different light scattering effects associated with the comparatively uneven paint surfaces.

A major use of painted exterior wood is in house claddings, where remediation costs may be high for wood exhibiting resin show-through. Consequently the wood processing industry's response to the issue of resin show-through is to avoid processing resinous wood for paint grades. Thus a significant volume of wood deemed resinous, is downgraded to lower value end uses.

It is an object of the present invention to provide improved or alternative treatments that substantially reduce or eliminate resin show-through in wood, particularly in wood normally considered too resinous for paint grades.

SUMMARY OF THE INVENTION

Accordingly, in one aspect the present invention relates to a composition to be applied to uncoated wood, preferably unpainted wood or unprimed wood comprising one or more autoxidative catalysts and a liquid carrier.

In another aspect the present invention relates to use of one or more autoxidative catalysts to reduce or prevent resin show-through in painted wood. In one embodiment, the one or more autoxidative catalysts are formulated with a liquid carrier as described below.

In another aspect the present invention relates to method of treating wood, including reducing or preventing resin show-through in painted wood, the method comprising applying one or more autoxidative catalysts to wood, preferably uncoated wood including unpainted wood or unprimed wood, including application before or during application of a primer coating to the wood.

In another aspect the present invention relates to wood treated according to a method of the invention.

Any of the following embodiments may relate to any of the above aspects, alone or in any combination of any two or more.

In one embodiment the treatment reduces or prevents resin show-through. In another embodiment the treatment reduces or prevents resin bleed. In yet another embodiment the treatment reduces or prevents resin show-through and resin bleed.

In one embodiment the one or more autoxidative catalysts is an oxidative drying agent such as a paint oxidative drying agent or paint autoxidative drier, such as a primary drier. In one embodiment the one or more autoxidative catalysts is an autoxidant such as a paint autoxidant. It should be understood that autoxidative catalysts useful herein are not limited to autoxidative catalysts that are paint driers.

In one embodiment the one or more autoxidative catalysts comprises one or more metal compounds. In one embodiment the autoxidative catalyst comprises one or more metal soaps of one or more carboxylic acids, one or more metal salts, or one or more metal coordination compounds or any combination of any two or more thereof.

In various embodiments the metal salt comprises an anion selected such that the metal salt is readily emulsified, dispersed or is substantially soluble in the chosen liquid carrier.

In one embodiment the one or more autoxidative catalysts comprises one or more metal soaps of one or more carboxylic acids.

In various embodiments the metal compound comprises cobalt, manganese, iron, cerium, vanadium, chromium, lead, zirconium, bismuth, nickel, copper, silver, or titanium, or any combination of any two or more thereof. In another embodiment the metal is cobalt, manganese, iron, cerium, vanadium, chromium, lead, zirconium, or bismuth, or any combination of any two or more thereof. In yet another embodiment the metal is cobalt, manganese, iron, cerium, vanadium or chromium, or any combination of any two or more thereof. In still another embodiment the metal is cobalt.

In various embodiments the metal compound comprises one or more carboxylate groups that comprise 1 to 10, 1 to 18, 1 to 20 or 1 to 24 carbon atoms and are selected from straight or branched chain molecules, optionally substituted with one or more groups selected from hydroxyl, methyl, ethyl, n-propyl, isopropyl, n-butyl, t-butyl, isobutyl, sec-butyl, and the like groups, preferably 1-6 or 1-4 such groups, and optionally comprising one or more double bonds or one or more triple bonds, preferably 1-4 such bonds, and from C5 to C7 cycloalkyl substituted with $[-(CH_2)_x-COO^-]_y$ where x is 1 to 5 and y is 1 or 2, optionally substituted with one or more groups selected from hydroxyl, methyl, ethyl, n-propyl, isopropyl, n-butyl, t-butyl, isobutyl, sec-butyl, and the like groups, preferably 1-4 such groups, and optionally comprising one or more double bonds or one or more triple bonds.

In one embodiment the carboxylate group is selected from formate (C1), acetate (C2), propanoate (C3), butanoate (C4), pentanoate (C5), hexanoate (C6), heptanoate (C7), octanoate (C8), nonanoate (C9), decanoate (C10), undecanoate (C11), dodecanoate (C12), tridecanoate (C13), tetradecanoate (C14), pentadecanoate (C15), hexadecanoate (C16), heptadecanoate (C17), octadecanoate (C18), nonadecanoate (C19), eicosanoate (C20), heneicosanoate (C21), docosanoate (C22), tricosanoate (C23), and tetracosanoate (C24) groups, optionally substituted with one or more groups selected from hydroxyl, methyl, ethyl, n-propyl, isopropyl, n-butyl, t-butyl, isobutyl, and sec-butyl groups, optionally unsaturated with one or more double bonds or one or more triple bonds, and any combination of any two or more thereof. The optional substituent(s) and double or triple bonds may be present at any position along the carbon chain.

In one embodiment the carboxylate group is selected from naphthenate derivatives, octoate derivatives such as 2-ethylhexanoate, and versatate derivatives such as neodecanoate.

In one embodiment the one or more autoxidative catalysts comprises cobalt-2-ethyl hexanoate, cobalt naphthenate, cobalt oleate, or cobalt acetate, or any combination of any two or more thereof. In another embodiment the one or more autoxidative catalysts comprises manganese-2-ethyl hexanoate. In another embodiment the one or more autoxidative catalysts comprises manganese-2-ethyl hexanoate, cobalt-2-ethyl hexanoate, cobalt naphthenate, cobalt oleate, or cobalt acetate, or any combination of any two or more thereof.

In another embodiment the metal salt is a bicarbonate, bromide, carbonate, chlorate, chloride, chromate, cyanide, dichromate, dihyrdogen phosphate, fluoride, halide, hydride, hydrogen phosphate, hydrogen sulphate, iodide, nitrate, nitride, nitrite, oxide, permanganate, phosphate, sulphate, sulphide, sulphite or thiocyanate salt, or any combination of any two or more thereof. Suitable oxides include alkoxides, such as, ethoxide, propoxide (including isopropoxide) and butoxide.

In one embodiment the metal salt is a cobalt salt, preferably cobalt chloride or cobalt sulphate, or any combination of any two or more thereof.

In various embodiments the concentration of the one or more autoxidative catalysts is at least about 0.05, 0.06, 0.07, 0.08, 0.09, 0.1, 0.11, 0.12, 0.13, 0.14, 0.15, 0.16, 0.17, 0.18, 0.19 or 0.2% by weight or more, and useful ranges may be selected between any of these values (for example, about 0.05 to about 0.2%).

In various embodiments the one or more autoxidative catalysts may be applied or formulated with one or more additional agents. In one embodiment the one or more additional agents are selected from one or more metallic or cationic coordination compounds, commonly used as secondary driers in paints, one or more auxiliary driers, or one or more wood treatment compounds, such as preservatives, water repellents, or fire retardants, or any combination of any two or more thereof.

In one embodiment the one or more secondary driers are selected from lead, zirconium, bismuth, barium, aluminum or strontium compounds, or any combination of any two or more thereof. The one or more secondary driers may be in the form of a metal soap, metal salt or metal coordination compound, as are known in the art, including those described above. In one embodiment the one or more secondary driers is an aluminium alkoxide, such as aluminium-isopropoxide, aluminium ethoxide or aluminium butoxide. In another embodiment the one or more secondary driers is an aluminium carboxylate, such as aluminium stearate or aluminium octoate.

In one embodiment the one or more auxiliary driers are selected from calcium, zinc, lithium or potassium compounds, or any combination of any two or more thereof. The one or more secondary driers may be in the form of a metal soap, metal salt or metal coordination compound, as are known in the art, including those described above.

In various embodiments the one or more autoxidative catalysts are delivered in a liquid carrier, and preferably liquid carrier is an aqueous or a non-aqueous carrier.

In one embodiment the aqueous carrier is water, a water-based wood preservative, a water-based primer (acrylic primer) or a water-based paint (acrylic paint). In a method of the invention, different carriers may be used in different application steps.

In one embodiment the water-based wood preservative is a copper solution, a fungicide solution such as a propiconazole-tebuconazole-imidicloprid (PTI) solution, or a borate solution, or any combination of any two or more thereof.

In one embodiment the non-aqueous carrier is an oil-based wood preservative, or a hydrocarbon-based carrier, or a combination thereof. In one embodiment the non-aqueous carrier is a light organic solvent preservative (LOSP), based on white spirit carrier and optionally including, for example, an azole-based active ingredient (such as propiconazole and/or tebuconazole) or tri-butyl tin naphthenate TBTN. Alternatively the carrier may be an ester, such as propyl acetate, butyl acetate, pentyl acetate or their isomers, such as tertiary butyl acetate.

In various embodiments the one or more autoxidative catalysts are in the form of a solution, a micro-emulsion, an emulsion or a dispersion.

In one embodiment the one or more autoxidative catalysts are substantially soluble in the liquid carrier. In one embodiment the one or more autoxidative catalysts are emulsified or dispersed in the liquid carrier.

In one embodiment the one or more autoxidative catalysts are applied to the wood by immersion, dipping, spraying, rolling, brushing, vacuum impregnation, pressure impregnation, vacuum/pressure impregnation, or any combination of any two or more thereof, or by any other means known in the art.

In one embodiment the one or more autoxidative catalysts are applied to the wood before, during or after application of a wood preservative to the wood. In another embodiment the one or more autoxidative catalysts are applied to the wood before, or during application of a primer coating to the wood.

In one embodiment the one or more autoxidative catalysts are applied to the wood at concentration of at least about 0.5, 1, 5, 10, 15, 20, 25, 30, 35, 40, 45 or 50 g/m$^3$ or more, and useful ranges may be selected between any of these values (for example, about 0.5 to about 50, about 8 to about 50, about 10 to about 50, about 20 to about 50, about 30 to about 50, or about 30 to about 40 g/m$^3$).

In various embodiments the wood comprises logs, processed timber and composite wood products such as plywood and laminated veneer lumber, whether treated with a preservative or not.

In one embodiment the wood is conifer. In one embodiment the wood is a resinous wood such as pine, particularly *Pinus radiata*.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

DETAILED DESCRIPTION OF THE INVENTION

It has been discovered that certain chemical compounds added to wood have beneficial effects in preventing resin show-through. Such chemicals may be conveniently added to the wood prior to painting, including addition to wood during priming.

1. Definitions

The term "autoxidative catalyst" refers to an agent capable of initiating or catalysing oxidation or polymerisation reactions of unsaturated carbon bonds of resin, fats and waxes or other polymerisable materials, including oxidation or polymerisation reactions in the presence of oxygen or UV radiation or both. Suitable autoxidative catalysts are reviewed by Gorkum, R. V., Bouwman, E., The oxidative drying of alkyd paint catalysed by metal complexes, Coord. Chem. Rev. (2005) 249:1709-1278, incorporated herein by reference. In various embodiments the autoxidative catalyst has two or more oxidation states or three or more oxidation states.

The term "comprising" as used in this specification means "consisting at least in part of" When interpreting statements in this specification which include that term, the features, prefaced by that term in each statement or claim, all need to be present but other features can also be present. Related terms such as "comprise" and "comprised" are to be interpreted in the same manner.

The phrase "resin show-through" refers to micro-blistering, bubbling, or in severe cases crocodiling (a crocodile skin appearance) of a painted surface. It is observed as paint shade differences revealing the resinous areas where the paint in the resinous areas appears bleached or washed out due to different light scattering effects associated with the comparatively uneven paint surfaces. Reference to "resin show-through" is also intended to include "resin bleed".

The phrase "resin bleed" refers to where wood resin may exude through a paint film to produce visible resin deposits on a painted surface.

The phrase "unpainted wood" refers to wood that may have had a primer or other pre-treatment applied but has not yet had a topcoat of paint applied.

2. Compositions of the Invention

A preferred chemical compound for inhibition of resin show-through is cobalt 2-ethyl hexanoate (also known as cobalt octoate)—an autoxidative catalyst. In Example 1 below, cobalt octoate was added to wood at an equivalent of 36 g (cobalt metal equivalent) per cubic meter of wood to produce a major reduction of resin show-through.

The mechanism or chemical pathway by which cobalt octoate inhibits resin show-through in wood has not been ascertained Cobalt octoate is used commercially as a paint drier in alkyd paint systems where it functions as a catalyst to promote resin autoxidation. Autoxidation is the direct reaction of oxygen with organic compounds to initiate free radical chain reactions, which lead to cross-linking and polymerization of the alkyd resin. A necessary requirement for autoxidation is the presence of unsaturated carbon bonds in the organic compound, but not all unsaturated compounds will autoxidise. Autoxidation of alkyd paint systems is described in detail by Gorkum, R. V., Bouwman, E., The oxidative drying of alkyd paint catalysed by metal complexes, Coord. Chem. Rev. (2005) 249:1709-1278, incorporated herein by reference.

Many of the wood extractives, such as resin acids, fatty acid esters and terpenes, which are concentrated in wood resinous areas, have unsaturated carbon bonding with potential for autoxidation in the presence of cobalt catalyst. Such autoxidation may cause loss of chemical reactivity and/or physical stabilization of the extractives, so that interactions between extractives and the paint system are minimized and resin show-through does not develop.

It may be predicted that other cobalt compounds capable of catalyzing autoxidation reactions, including, but not limited to, cobalt naphthenate, cobalt oleate and cobalt acetate may also be useful in preventing resin show-through.

Other autoxidative paint driers may also prove beneficial in controlling resin show-through. Other metals capable of autoxidation in alkyd paint systems include compounds of iron, copper, manganese, titanium, vanadium and cerium.

Autoxidative paint driers are commonly used in conjunction with secondary driers, incapable of autoxidation, to enhance crosslinking. The most commonly used secondary driers include compounds of aluminium, zirconium, zinc, calcium, lithium and potassium compounds. In particular, aluminium compounds, in conjunction with cobalt driers, greatly enhance crosslinking and produce films of significantly increased hardness. Secondary driers are reviewed by Gorkum, R. V., Bouwman, E., The oxidative drying of alkyd paint catalysed by metal complexes, Coord. Chem. Rev. (2005) 249:1709-1278, incorporated herein by reference.

A preferred method of adding such chemicals to wood is in conjunction the wood preservative treatment, such as LOSP (light organic solvent preservative). Pine timber for exterior outdoor uses in NZ and Australia must be impregnated with chemical preservatives according to the relevant standards. For exterior paint grades, such as weatherboards, the most common treatment process is LOSP. This process utilizes white spirit as a carrier fluid for the active ingredients and impregnation produces no significant wood swelling, which is particularly advantageous for wood products which are dimensionally finished or profiled before treatment. After LOSP treatment, the wood is conditioned to allow evaporation of the white spirit from the wood.

Although LOSP treatment is a commonly used wood preservative method for paint grade products, there exist alternative low uptake water based systems which allow diffusion of borate salts or emulsified triazole compounds. The metal catalysed autoxidation reactions are not limited to hydrocarbon solvent (white spirit) systems and therefore there is expected benefit in the addition of water solubilised or emulsified cobalt and/or other catalysts in such preservative formulations.

Most primers used for painting exterior wood products are based on alkyd resin systems and as such, already contain suitable concentrations of cobalt and/or other primary driers and auxiliary driers to achieve optimal through drying of the coat. Drying rate issues may limit the addition of excess quantities of driers to alkyd resin systems.

In contrast, acrylic primer systems, which are water emulsified and not cross linking, may accommodate metal based driers, which may precipitate in the surface layers of the wood. It is possible that some benefit in reducing show-through may accrue from this approach.

The afore-mentioned methods of incorporating autoxidative catalysts and additional agents into wood via either the preservative fluid or primer composition have cost advantages because no additional wood processing steps are required. In some instances however, it may be advantageous to introduce the autoxidative catalysts and additional agents independently as, for instance, in a pre-primer application. This strategy may remove any formulation constraints imposed by the nature of the preservative fluid or primer compositions, and provide flexibility in terms of application method, which may include treating the wood by pressure and/or vacuum impregnation, dipping, spraying, roller, brush or other means, with the treatment composition.

Various aspects of the invention will now be illustrated in non-limiting ways by reference to the following examples.

EXAMPLES

Example 1

Eighteen highly resinous shooks, 90 mm×19 mm×400 mm, were selected for resin show-through trials, where the following three LOSP treatments were compared.
(a) An azole based LOSP formulation, containing 0.6% tebuconazole, 0.6% propiconazole, 0.45% permethrin and 3% total resins and waxes in a predominantly white spirit solvent.
(b) A tri-butyl tin naphthenate (TBTN) based LOSP formulation containing an equivalent 1.3% tin, 0.45% permethrin and 3% resins and waxes.
(c) An azole formulation as above but also containing 0.12% (w/v) equivalent cobalt content (added as 2% of a 6% cobalt octoate solution).

After LOSP impregnation with fluid uptakes of 30 L/m$^3$, the shooks were air conditioned for five days to remove solvent, primed with a commercial alkyd primer, conditioned seven days and painted with two exterior acrylic topcoats of light reflective value (LRF) of 35.

After further conditioning (minimum one week) the shooks were mounted on plywood sheets angled 45 degrees towards maximum sunlight during the summer months. Under these conditions board surface temperatures generally ranged between 15 and 55° C.

The evaluation of resin show-through after 12 weeks exposure of the boards is shown in Table 1. The results clearly show the beneficial effect of the cobalt octoate additive where none of the shooks exhibited resin show-through, whereas a majority of the boards in the two "standard" treatments exhibited some show-through.

TABLE 1

Twelve Week Resin Show-through Evaluation of Different LOSP Treatments

| LOSP Treatment Solution | Unaffected | Minor Show-through | Major Show-through |
| --- | --- | --- | --- |
| Azole | 2 | 3 | 1 |
| TBTN | 1 | 5 | 0 |
| Azole + 0.12% Co octoate | 6 | 0 | 0 |

After 18 months exposure the shooks were re-evaluated for show-through and the results are shown in Table 2. The results confirm the longer term effectiveness of the cobalt octoate treatment.

TABLE 2

Comparison of LOSP treatments after 18 months

| Treatment Solution | Unaffected | Minor Show-through | Major Show-through |
| --- | --- | --- | --- |
| Std LOSP azole | 0 | 1 | 5 |
| LOSP (TBTN) | 0 | 1 | 5 |
| Azole + 0.12% cobalt octoate | 6 | 0 | 0 |

Example 2

An accelerated weathering test using a QUV weatherometer (Manufacturer—Q Panel Lab. Products, Cleveland, Ohio, USA) was devised for investigations of resin show-through. This test consisted of a two-stage four-hourly alternating cycle of the following.

An ultraviolet heating stage using short wavelength, UVB −313 nm radiation, where irradiance was controlled at 50% maximum by the four UV sensors. An air blower operates during the UV cycle and the temperature was controlled at 55° C.

A condensation cycle where the UV lamps are off and the temperature is controlled at 40° C. by water heated in an underneath tray. In this cycle the board surfaces are continually wet once condensation is fully developed (after about one hour).

The QUV sample positions were adapted to hold up to 24 shooks (310 mm×90 mm) in the unit. Generally QUV exposures of 250-300 hours were sufficient to allow strong development of resin show-through in resinous shooks.

A comparison of QUV exposures of shooks treated by the standard azole formulation and the same formulation with cobalt octoate added, as described in Example 1, is shown in Table 3. After LOSP treatment the shooks were conditioned, primed and top-coated as in Example 1.

TABLE 3

Resin Show-through in QUV trials of Azole Treatments with and without Cobalt Octoate.

| LOSP Treatment | Unaffected | Minor Show-through | Major Show-through |
|---|---|---|---|
| Azole | 1 | 3 | 8 |
| Azole + Co octoate | 8 | 2 | 2 |

The QUV results support the finding of the outdoor exposure trial outlined in Example 1, that the presence of cobalt octoate has a major beneficial effect on the inhibition of resin show-through.

Example 3

A larger scale exposure trial involving outdoor weathering of 850 resinous shooks distributed over five sites with differing local climates was undertaken to establish the effectiveness of cobalt octoate treatment. The shooks were cut to 300-350 mm long and finger-jointed to produce 6 m lengths.

After moulding and longitudinally splitting into halves, the 6 m lengths of 90 mm×18 mm pieces were re-examined to cull insufficiently resinous pieces or defects such as resin pockets, splits or knots. Finally 252 pieces of lengths 1.0-1.2 m were selected for the trial. Each length contained either three or four shooks or about 850 shooks in total.

A pilot LOSP treatment plant, void volume 200 L and length 1.2 m was used for the trials. The average fluid uptake for the cobalt treatments was 27.3 L/m$^3$ corresponding to a cobalt additive concentration of 32 g/m3 of wood. After treatment, the lengths were conditioned in fillet for eight days to remove solvent before priming with a commercial alkyd primer After a further 12 day conditioning period two coats of commercial semi-gloss exterior, acrylic topcoats were applied as described in Examples 1 and 2.

The boards were backed with bitumen tape to prevent egress of water from trapped water behind the boards. The boards were attached to plywood panels (12 per panel) which were oriented in sunny positions approximately north at angles 45-60°.

Five different NZ sites ranging from the north of the North Island to the south of the South Island, New Zealand, both coastal and inland, to encompass differing temperatures and rainfall conditions.

Inspections were made after six months exposure including a summer period. Three categories of resin show-through were distinguished: Major show-through—sufficiently evident to be unacceptable in a commercial situation; Minor show-through—evident on close inspection by an experienced observer; None.

The results of the field trial assessments, shown in Table 4, confirm the efficacy of the cobalt octoate treatment.

TABLE 4

Comparison of Standard and Cobalt additive Treated Boards at Five Sites

| Treatment | Total Boards Exhibiting Show-through | |
|---|---|---|
| Location | STD LOSP | +32 g/m$^3$ Cobalt |
| Central coastal | 5 major 10 minor | 0 |
| Central | 8 major | 0 |
| inland | 9 minor | |
| Northern coastal | 7 major 2 minor | 1 minor |
| Southern coastal | 8 major 7 minor | 2 minor |
| Southern inland | 3 major 5 minor | 0 |

Example 4

An accelerated weathering trial was carried under similar conditions to Example 2, to determine the efficacy of lower levels of the cobalt octoate additive. The results, shown in Table 5, indicate positive benefit at the higher levels of 9 g/m$^3$ and 36 g/m$^3$ cobalt contents in the wood.

TABLE 5

Effect of lower Cobalt levels.

| Treatment | Primer | No of Shooks | % Shooks with Show-through | | |
|---|---|---|---|---|---|
| | | | None | Minor | Major |
| LOSP | Alkyd | 4 | 25 | 25 | 50 |
| LOSP + 3.6 g/m$^3$ Co | Alkyd | 6 | 33 | 17 | 50 |
| LOSP + 9 g/m$^3$ Co | Alkyd | 6 | 33 | 50 | 17 |
| LOSP + 36 g/m$^3$ Co | Alkyd | 6 | 83 | 0 | 17 |

Example 5

An accelerated weathering trial under similar conditions to Example 2 was carried out to determine if the cobalt treatment would be effective for acrylic primed systems. Ten shooks treated with standard LOSP and (two coats) of acrylic primer were compared to ten similarly treated shooks but with cobalt octoate additive in the LOSP fluid to produce an equivalent cobalt concentration of 36 g/m$^3$ in the wood. Both sets (and all sets in this research) were top coated with two coats of exterior acrylic.

TABLE 6

Effect of Cobalt in Acrylic Primed Systems

| Treatment | Prime | No of Shooks | % Shooks with Show-through | | |
|---|---|---|---|---|---|
| | | | None | Minor | Major |
| LOSP | Acrylic | 10 | 40 | 40 | 20 |
| LOSP + 36 g/m$^3$ cobalt octoate | Acrylic | 10 | 30 | 70 | 0 |

Further Examples

A further six accelerated weathering trials were carried out at a higher weathering temperature (5° C. hotter) and longer weathering period (extended two days) to provide a greater challenge to the treatments compared to Examples 2, 4 and 5, which showed only minor differences between treatments. The results of the six trials are shown in Table 7.

provide a similar level of cobalt uptake by the wood The results, shown in Table 7, indicated the solvent based cobalt octoate pre-primer provided more reduction of show-through than the aqueous cobalt treatment.

TABLE 7

QUV Results of Further Six Trials.

| Example/ Trial set | Treatment | Pre-prime | Prime | No of Shooks | % Shooks with Show-through | | |
|---|---|---|---|---|---|---|---|
| | | | | | None | Minor | Major |
| Reference | LOSP | — | Alkyd | 21 | 10 | 20 | 71 |
| Reference | LOSP + 36 g/m³ Cobalt | — | Alkyd | 22 | 50 | 32 | 18 |
| Example 6 | LOSP + 18 g/m³ Cobalt | — | Alkyd | 9 | 33 | 22 | 44 |
| Example 7 | Borate | — | Alkyd | 8 | 13 | 38 | 50 |
| Example 7 | Borate + 36 g/m³ cobalt (emulsion) | | | 8 | 63 | 38 | — |
| Example 8 | LOSP | Aq-Co-sulphate | Alkyd | 16 | 6 | 13 | 81 |
| Example 8 | LOSP | Cobalt octoate | Alkyd | 8 | — | 63 | 38 |
| Example 9 | Presso | — | Alkyd | 9 | 33 | 33 | 33 |
| Example 9 | Presso 36 g/m³ Cobalt | — | Alkyd | 9 | 56 | 33 | 11 |
| Example 10 | LOSP + 36 g/m³ Mn-octoate | — | Alkyd | 7 | 57 | 28 | 14 |
| Example 11 | LOSP + Al isopropoxide | — | Alkyd | 7 | 14 | 43 | 43 |
| Example 11 | LOSP + Al isopropoxide + 36 g/m³ Cobalt | — | Alkyd | 7 | 71 | 28 | 0 |

Example 6

Example 6 investigated an intermediate concentration of the cobalt octoate additive at 18 g/m³ of wood. The results, shown in Table 7, indicate an effectiveness intermediate between no cobalt and the higher level of cobalt of 36 g/m³

Example 7

Example 7 investigated the efficacy of the cobalt additive in aqueous borate preservative systems. Eight shooks treated by an aqueous borate process were compared with eight shooks similarly treated but with the addition of emulsified cobalt octoate in the borate fluid (to attain 36 g/m³ cobalt in the wood. After borate treatment and conditioning the shooks were alkyd primed and acrylic top coated according to earlier trials. The results, shown in Table 7, indicated a beneficial effect in reducing show-through by the presence of cobalt in the borate fluid.

Example 8

Example 8 aimed to determine if cobalt could be effectively applied as a pre-primer treatment instead of incorporation in treatment fluids. This option would allow a targeted approach whereby LOSP treated resinous wood could be segregated and coated with a pre-primer prior to the standard primer process.

Eight shooks were LOSP treated and pre-primed with diluted (in white spirit) cobalt octoate solution to provide a cobalt level of 36 g/m³ in the wood, similar to the quantity taken up in the LOSP treatments. After pre-priming the shooks were alkyd primed and acrylic top coated as in previous trials. A second set of sixteen shooks was pre-primed with an aqueous solution of cobalt sulphate to

Example 9

Example 9 aimed to determine if the cobalt octoate additive would be effective in an alternative solvent system which uses tertiary butyl acetate instead of white spirit as a carrier solvent. This system is known as the "Presso Process"—ref—*"Wood Treatment Using Ester Compounds as Recoverable Carrier Solvents"* by F W Fraer and R C Eddy—*Proc. American Wood Preservers Association*, Annual Meeting Nashville Tenn., USA., May 2012.

Nine shooks were treated by the standard Presso fluid, which contains the same actives as standard LOSP. A further nine shooks were treated with standard Presso fluid containing 2% cobalt octoate. As shown in Table 7, both Presso treatments exhibited less resin show-through than the standard LOSP treatment. The presence of cobalt marginally improved the performance of the Presso treatment in controlling show-through.

Example 10

Example 10 evaluated manganese octoate as an alternative to cobalt octoate for reduction of resin show-through. Seven shooks with manganese octoate incorporated into the LOSP fluid to give an equivalent concentration of 36 g/m³ in the wood were compared to LOSP treatments with and without cobalt octoate.

The results, shown in Table 7, indicated a reduction in show-through for the manganese octoate doped LOSP treatment. The reduction in show-through was similar to the equivalent cobalt octoate treatment.

Example 11

Example 11 aimed to determine if the combination of cobalt and aluminium driers could produce increased benefit in controlling show-through. As a source of organically soluble aluminium for this trial, aluminium isopropoxide was pre-dissolved in xylene (50 g/L) and the solution added to the LOSP fluid to generate a solution of 1 g/L aluminium in the fluid or 30 $g/m^3$ in the treated wood. The trial consisted of 7 shooks treated in LOSP fluid with the Al drier only.

7 shooks treated in LOSP fluid with cobalt octoate only (36 $g/m^3$) only.

7 shooks treated with the combination of the above Al and cobalt octoate additives.

The results indicate that aluminium drier alone is not effective in preventing resin show-through. However the combination of aluminium and cobalt driers gave a very good result.

INDUSTRIAL APPLICABILITY

The present invention relates to compositions for treating wood, and in particular to compositions and their use for reducing or preventing resin show-through or resin-bleed or resin show-through and resin-bleed, particularly in pine. These compositions have application in the building and decorating industries.

Those persons skilled in the art will understand that the above description is provided by way of illustration only and that the invention is not limited thereto.

What is claimed is:

1. A method of reducing or preventing resin show-through in painted wood, the method comprising:
    impregnating unprimed, unpainted wood at a concentration of 8 to 50 $g/m^3$ with one or more autoxidative catalysts in a liquid carrier before application of a primer coating to the wood, the one or more autoxidative catalysts comprising one or more metal compounds selected from one or more cobalt compounds, one or more manganese compounds, one or more cerium compounds, one or more vanadium compounds, or a combination of any two or more thereof, the liquid carrier comprising a water-based wood preservative, or a non-aqueous carrier, the wood being pine
    to reduce or prevent resin show-through in the wood after painting.

2. The method of claim 1, wherein the one or more autoxidative catalysts is an oxidative drying agent.

3. The method of claim 1, wherein the one or more metal compounds comprise one or more metal soaps of one or more carboxylic acids, one or more metal salts, or one or more metal coordination compounds, or any combination of any two or more thereof.

4. The method of claim 1, wherein the one or more metal compounds comprise cobalt or manganese, or a combination thereof.

5. The method of claim 1, wherein the one or more metal compounds comprises one or more carboxylate groups.

6. The method of claim 5, wherein the carboxylate group is selected from formate (C1), acetate (C2), propanoate (C3), butanoate (C4), pentanoate (C5), hexanoate (C6), heptanoate (C7), octanoate (C8), nonanoate (C9), decanoate (C10), undecanoate (C11), dodecanoate (C12), tridecanoate (C13), tetradecanoate (C14), pentadecanoate (C15), hexadecanoate (C16), heptadecanoate (C17), octadecanoate (C18), nonadecanoate (C19), eicosanoate (C20), heneicosanoate (C21), docosanoate (C22), tricosanoate (C23), and tetracosanoate (C24) groups, optionally substituted with one or more groups selected from hydroxyl, methyl, ethyl, n-propyl, isopropyl, n-butyl, t-butyl, isobutyl, and sec-butyl groups, optionally unsaturated with one or more double or triple bonds, and any combination of any two or more thereof.

7. The method of claim 1, wherein the one or more autoxidative catalysts comprises manganese-2-ethyl hexanoate, cobalt-2-ethyl hexanoate, cobalt napthenate, cobalt oleate, or cobalt acetate, or any combination of any two or more thereof.

8. The method of claim 3, wherein the one or more metal compounds comprise one or more metal salts selected from cobalt chloride or cobalt sulphate, or a combination thereof.

9. The method of claim 1, wherein the one or more autoxidative catalysts is applied or formulated with one or more secondary driers, one or more auxiliary driers, or one or more wood preservative compounds, or any combination of any two or more thereof.

10. The method of claim 9, wherein the one or more autoxidative catalysts is applied or formulated with one or more secondary driers selected from lead, zirconium, bismuth, barium, aluminum or strontium compounds, or any combination of any two or more thereof.

11. The method of claim 10, wherein the one or more autoxidative catalysts is applied or formulated with one or more secondary driers selected from an aluminium oxide and an aluminium carboxylate or a combination thereof.

12. The method of claim 1, wherein the liquid carrier is a non-aqueous carrier selected from an oil-based wood preservative, a hydrocarbon-based carrier, a light organic solvent preservative (LOSP), and an ester solution, or a combination thereof.

13. The method of claim 1, wherein the water-based wood preservative comprises a borate or triazole.

14. The method of claim 1, wherein the one or more autoxidative catalysts are impregnated into wood at concentration of about 20 to about 50 $g/m^3$ on a metal-equivalent basis.

15. The method of claim 1, wherein the wood comprises logs, processed timber or composite wood products.

16. The method of claim 1, wherein the unprimed, unpainted wood is impregnated with the one or more autoxidation catalysts at a concentration of 10 to 50 $g/m^3$.

17. The method of claim 1, wherein the unprimed, unpainted wood is impregnated with the one or more autoxidation catalysts at a concentration of 20 to 50 $g/m^3$.

18. A method of reducing or preventing resin show-through in painted wood, the method comprising
    impregnating unprimed, unpainted wood by vacuum impregnation, pressure impregnation, or vacuum/pressure impregnation at a concentration of 8 to 50 $g/m^3$ with one or more autoxidative catalysts in a liquid carrier, the one or more autoxidative catalysts comprising one or more metal compounds selected from one or more cobalt compounds, one or more manganese compounds, one or more cerium compounds, one or more vanadium compounds, or a combination of any two or more thereof, the wood being pine,
    the liquid carrier comprising a water-based wood preservative, or a non-aqueous carrier
    to reduce or prevent resin show-through in the wood after painting.

19. The method of claim 18, wherein the liquid carrier is a non-aqueous carrier selected from an oil-based wood preservative, a hydrocarbon-based carrier, a light organic solvent preservative (LOSP), and an ester solution, or a combination thereof.

20. The method of claim 18, wherein the water-based wood preservative comprises a borate or triazole.

21. The method of claim 18, wherein the one or more metal compounds impregnated into the wood comprise cobalt or manganese, or a combination thereof.

22. The method of claim 21, wherein the one or more metal compounds are impregnated into the wood at concentration of about 20 to about 50 $g/m^3$ on a metal-equivalent basis.

23. The method of claim 18, wherein the unprimed, unpainted wood is impregnated with the one or more autoxidation catalysts at a concentration of 10 to 50 $g/m^3$.

24. The method of claim 18, wherein the unprimed, unpainted wood is impregnated with the one or more autoxidation catalysts at a concentration of 20 to 50 $g/m^3$.

25. A method of reducing or preventing resin show-through in painted wood, the method comprising
impregnating unprimed, unpainted wood with one or more autoxidative catalysts at a concentration of 8 to 50 $g/m^3$, the one or more autoxidative catalysts comprising one or more metal compounds selected from one or more cobalt compounds, one or more manganese compounds, one or more cerium compounds, one or more vanadium compounds, or a combination of any two or more thereof, the wood being pine, and
applying a primer coating to the impregnated wood to reduce or prevent resin show-through in the wood after painting.

26. The method of claim 25, wherein the one or more metal compounds impregnated into the wood comprise cobalt or manganese, or a combination thereof.

27. The method of claim 26, wherein the one or more metal compounds are impregnated into the wood at concentration of about 20 to about 50 $g/m^3$ on a metal-equivalent basis.

28. The method of claim 27, wherein the one or more metal compounds are impregnated into the wood in a liquid carrier selected from water, a water-based wood preservative, and a non-aqueous carrier.

29. The method of claim 25, wherein the unprimed, unpainted wood is impregnated with the one or more autoxidation catalysts at a concentration of 10 to 50 $g/m^3$.

30. The method of claim 25, wherein the unprimed, unpainted wood is impregnated with the one or more autoxidation catalysts at a concentration of 20 to 50 $g/m^3$.

* * * * *